(12) United States Patent
Morris et al.

(10) Patent No.: US 7,588,642 B1
(45) Date of Patent: Sep. 15, 2009

(54) ABLUMINAL STENT COATING APPARATUS AND METHOD USING A BRUSH ASSEMBLY

(75) Inventors: Grayson Morris, San Francisco, CA (US); Svava Maria Atladottir, San Francisco, CA (US); Carla Pienknagura, San Francisco, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 678 days.

(21) Appl. No.: 10/999,829

(22) Filed: Nov. 29, 2004

(51) Int. Cl.
*B05C 1/06* (2006.01)

(52) U.S. Cl. ............... 118/663; 118/664; 118/665; 118/670; 118/681; 118/712; 118/264

(58) Field of Classification Search ............... 118/663, 118/664, 665, 670, 681, 712, 264, 403; 427/429; 15/21.1, 88.1, 88.2
See application file for complete search history.

(56) References Cited

U.S. PATENT DOCUMENTS

| | | | |
|---|---|---|---|
| 4,329,383 A | 5/1982 | Joh | |
| 4,733,665 A | 3/1988 | Palmaz | |
| 4,800,882 A | 1/1989 | Gianturco | |
| 4,882,168 A | 11/1989 | Casey et al. | |
| 4,886,062 A | 12/1989 | Wiktor | |
| 4,941,870 A | 7/1990 | Okada et al. | |
| 4,967,606 A | 11/1990 | Wells et al. | |
| 4,977,901 A | 12/1990 | Ofstead | |
| 5,112,457 A | 5/1992 | Marchant | |
| 5,165,919 A | 11/1992 | Sasaki et al. | |
| 5,225,750 A | 7/1993 | Higuchi et al. | |
| 5,272,012 A | 12/1993 | Opolski | |
| 5,292,516 A | 3/1994 | Viegas et al. | |
| 5,298,260 A | 3/1994 | Viegas et al. | |
| 5,300,295 A | 4/1994 | Viegas et al. | |
| 5,306,501 A | 4/1994 | Viegas et al. | |
| 5,328,471 A | 7/1994 | Slepian | |
| 5,330,768 A | 7/1994 | Park et al. | |
| 5,380,299 A | 1/1995 | Fearnot et al. | |
| 5,417,981 A | 5/1995 | Endo et al. | |
| 5,447,724 A | 9/1995 | Helmus et al. | |
| 5,455,040 A | 10/1995 | Marchant | |
| 5,462,990 A | 10/1995 | Hubbell et al. | |

(Continued)

FOREIGN PATENT DOCUMENTS

EP 0 301 856 2/1989

(Continued)

OTHER PUBLICATIONS

Anonymous, *Cardiologists Draw—Up The Dream Stent*, Clinica 710:15 (Jun. 17, 1996), http://www.dialogweb.com/cgi/document?req=1061848202959, printed Aug. 25, 2003 (2 pages).

(Continued)

*Primary Examiner*—Laura Edwards
(74) *Attorney, Agent, or Firm*—Squire, Sanders & Dempsey L.L.P.

(57) ABSTRACT

The apparatus and method use an optical feedback system to align a brush assembly with a stent strut. Once alignment is achieved, a coating is dispensed onto the stent strut via the brush assembly and the brush assembly is moved along the stent strut to coat the stent strut.

24 Claims, 5 Drawing Sheets

U.S. PATENT DOCUMENTS

| | | | |
|---|---|---|---|
| 5,464,650 A | 11/1995 | Berg et al. | |
| 5,527,337 A | 6/1996 | Stack et al. | |
| 5,569,463 A | 10/1996 | Helmus et al. | |
| 5,578,073 A | 11/1996 | Haimovich et al. | |
| 5,605,696 A | 2/1997 | Eury et al. | |
| 5,609,629 A | 3/1997 | Fearnot et al. | |
| 5,624,411 A | 4/1997 | Tuch | |
| 5,628,730 A | 5/1997 | Shapland et al. | |
| 5,649,977 A | 7/1997 | Campbell | |
| 5,658,995 A | 8/1997 | Kohn et al. | |
| 5,667,767 A | 9/1997 | Greff et al. | |
| 5,670,558 A | 9/1997 | Onishi et al. | |
| 5,679,400 A | 10/1997 | Tuch | |
| 5,700,286 A | 12/1997 | Tartaglia et al. | |
| 5,702,754 A | 12/1997 | Zhong | |
| 5,713,949 A | 2/1998 | Jayaraman | |
| 5,716,981 A | 2/1998 | Hunter et al. | |
| 5,735,897 A | 4/1998 | Buirge | |
| 5,746,998 A | 5/1998 | Torchilin et al. | |
| 5,766,710 A | 6/1998 | Turnlund et al. | |
| 5,769,883 A | 6/1998 | Buscemi et al. | |
| 5,776,184 A | 7/1998 | Tuch | |
| 5,788,979 A | 8/1998 | Alt et al. | |
| 5,800,392 A | 9/1998 | Racchini | |
| 5,820,917 A | 10/1998 | Tuch | |
| 5,824,048 A | 10/1998 | Tuch | |
| 5,824,049 A | 10/1998 | Ragheb et al. | |
| 5,824,056 A | 10/1998 | Rosenberg | |
| 5,830,178 A | 11/1998 | Jones et al. | |
| 5,837,008 A | 11/1998 | Berg et al. | |
| 5,837,313 A | 11/1998 | Ding et al. | |
| 5,843,172 A | 12/1998 | Yan | |
| 5,851,508 A | 12/1998 | Greff et al. | |
| 5,858,746 A | 1/1999 | Hubbell et al. | |
| 5,865,814 A | 2/1999 | Tuch | |
| 5,869,127 A | 2/1999 | Zhong | |
| 5,873,904 A | 2/1999 | Ragheb et al. | |
| 5,876,433 A | 3/1999 | Lunn | |
| 5,877,224 A | 3/1999 | Brocchini et al. | |
| 5,925,720 A | 7/1999 | Kataoka et al. | |
| 5,955,509 A | 9/1999 | Webber et al. | |
| 5,971,954 A | 10/1999 | Conway et al. | |
| 5,972,505 A | 10/1999 | Phillips et al. | |
| 5,980,928 A | 11/1999 | Terry | |
| 5,980,972 A | 11/1999 | Ding | |
| 5,997,517 A | 12/1999 | Whitbourne | |
| 6,010,530 A | 1/2000 | Goicoechea | |
| 6,015,541 A | 1/2000 | Greff et al. | |
| 6,033,582 A | 3/2000 | Lee et al. | |
| 6,042,875 A | 3/2000 | Ding et al. | |
| 6,051,576 A | 4/2000 | Ashton et al. | |
| 6,051,648 A | 4/2000 | Rhee et al. | |
| 6,056,993 A * | 5/2000 | Leidner et al. | 427/2.25 |
| 6,060,451 A | 5/2000 | DiMaio et al. | |
| 6,060,518 A | 5/2000 | Kabanov et al. | |
| 6,080,488 A | 6/2000 | Hostettler et al. | |
| 6,096,070 A | 8/2000 | Ragheb et al. | |
| 6,099,562 A | 8/2000 | Ding et al. | |
| 6,110,188 A | 8/2000 | Narciso, Jr. | |
| 6,110,483 A | 8/2000 | Whitbourne et al. | |
| 6,113,629 A | 9/2000 | Ken | |
| 6,120,536 A | 9/2000 | Ding et al. | |
| 6,120,904 A | 9/2000 | Hostettler et al. | |
| 6,121,027 A | 9/2000 | Clapper et al. | |
| 6,129,761 A | 10/2000 | Hubbell | |
| 6,153,252 A | 11/2000 | Hossainy et al. | |
| 6,165,212 A | 12/2000 | Dereume et al. | |
| 6,203,551 B1 | 3/2001 | Wu | |
| 6,209,621 B1 | 4/2001 | Treacy | |
| 6,214,407 B1 | 4/2001 | Laube et al. | |
| 6,231,600 B1 | 5/2001 | Zhong | |
| 6,240,616 B1 | 6/2001 | Yan | |
| 6,245,753 B1 | 6/2001 | Byun et al. | |
| 6,251,136 B1 | 6/2001 | Guruwaiya et al. | |
| 6,254,632 B1 | 7/2001 | Wu et al. | |
| 6,258,121 B1 | 7/2001 | Yang et al. | |
| 6,283,947 B1 | 9/2001 | Mirzaee | |
| 6,283,949 B1 | 9/2001 | Roorda | |
| 6,284,305 B1 | 9/2001 | Ding et al. | |
| 6,287,628 B1 | 9/2001 | Hossainy et al. | |
| 6,299,604 B1 | 10/2001 | Ragheb et al. | |
| 6,306,176 B1 | 10/2001 | Whitbourne | |
| 6,331,313 B1 | 12/2001 | Wong et al. | |
| 6,335,029 B1 | 1/2002 | Kamath et al. | |
| 6,346,110 B2 | 2/2002 | Wu | |
| 6,358,556 B1 | 3/2002 | Ding et al. | |
| 6,375,459 B1 * | 4/2002 | Kamen et al. | 433/80 |
| 6,379,381 B1 | 4/2002 | Hossainy et al. | |
| 6,395,326 B1 | 5/2002 | Castro et al. | |
| 6,419,692 B1 | 7/2002 | Yang et al. | |
| 6,451,373 B1 | 9/2002 | Hossainy et al. | |
| 6,494,862 B1 | 12/2002 | Ray et al. | |
| 6,503,556 B2 | 1/2003 | Harish et al. | |
| 6,503,954 B1 | 1/2003 | Bhat et al. | |
| 6,506,437 B1 | 1/2003 | Harish et al. | |
| 6,527,801 B1 | 3/2003 | Dutta | |
| 6,527,863 B1 | 3/2003 | Pacetti et al. | |
| 6,540,776 B2 | 4/2003 | Sanders Millare et al. | |
| 6,544,223 B1 | 4/2003 | Kokish | |
| 6,544,543 B1 | 4/2003 | Mandrusov et al. | |
| 6,544,582 B1 | 4/2003 | Yoe | |
| 6,555,157 B1 | 4/2003 | Hossainy | |
| 6,558,733 B1 | 5/2003 | Hossainy et al. | |
| 6,565,659 B1 | 5/2003 | Pacetti et al. | |
| 6,572,644 B1 | 6/2003 | Moein | |
| 6,585,765 B1 | 7/2003 | Hossainy et al. | |
| 6,585,926 B1 | 7/2003 | Mirzaee | |
| 6,605,154 B1 | 8/2003 | Villareal | |
| 7,204,110 B2 * | 4/2007 | Hammar et al. | 72/40 |
| 2001/0018469 A1 | 8/2001 | Chen et al. | 523/121 |
| 2001/0037145 A1 | 11/2001 | Guruwaiya et al. | 623/1.15 |
| 2002/0077693 A1 | 6/2002 | Barclay et al. | 623/1.13 |
| 2002/0091433 A1 | 7/2002 | Ding et al. | 623/1.2 |
| 2002/0155212 A1 | 10/2002 | Hossainy | 427/2.25 |
| 2003/0065377 A1 | 4/2003 | Davila et al. | 623/1.13 |
| 2003/0099712 A1 | 5/2003 | Jayaraman | 424/486 |
| 2003/0157243 A1 * | 8/2003 | Trabold et al. | 427/8 |

FOREIGN PATENT DOCUMENTS

| | | |
|---|---|---|
| EP | 0 514 406 | 11/1992 |
| EP | 0 604 022 | 6/1994 |
| EP | 0 623 354 | 11/1994 |
| EP | 0 665 023 | 8/1995 |
| EP | 0 701 802 | 3/1996 |
| EP | 0 716 836 | 6/1996 |
| EP | 0 809 999 | 12/1997 |
| EP | 0 832 655 | 4/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 273 314 | 1/2003 |
| JP | 2001-190687 | 7/2001 |
| WO | WO 91/12846 | 9/1991 |
| WO | WO 95/10989 | 4/1995 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/17331 | 4/1998 |

| | | |
|---|---|---|
| WO | WO 98/23228 | 6/1998 |
| WO | WO 98/36784 | 8/1998 |
| WO | WO 99/01118 | 1/1999 |
| WO | WO 99/38546 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/64506 | 11/2000 |
| WO | WO 01/01890 | 1/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/74414 | 10/2001 |
| WO | WO 02/03890 | 1/2002 |
| WO | WO 02/26162 | 4/2002 |
| WO | WO 02/34311 | 5/2002 |
| WO | WO 02/056790 | 7/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |

OTHER PUBLICATIONS

Anonymous, *Heparin-coated stents cut complications by 30%*, Clinica 732:17 (Nov. 18, 1996), http://www.dialogweb.com/cgi/document?req=1061847871753, printed Aug. 25, 2003 (2 pages).

Anonymous, *Rolling Therapeutic Agent Loading Device for Therapeutic Agent Delivery or Coated Stent* (Abstract 434009), Res. Disclos. pp. 974-975 (Jun. 2000).

Anonymous, *Stenting continues to dominate cardiology*, Clinica 720:22 (Sep. 2, 1996), http://www.dialogweb.com/cgi/document?req=1061848017752, printed Aug. 25, 2003 (2 pages).

Aoyagi et al., *Preparation of cross-linked aliphatic polyester and application to thermo-responsive material*, Journal of Controlled Release 32:87-96 (1994).

Barath et al., *Low Dose of Antitumor Agents Prevents Smooth Muscle Cell Proliferation After Endothelial Injury*, JACC 13(2): 252A (Abstract) (Feb. 1989).

Barbucci et al., *Coating of commercially available materials with a new heparinizable material*, J. Biomed. Mater. Res. 25:1259-1274 (Oct. 1991).

Capillary Action, http://www.ndt-ed.org/EducationResources/CommunityCollege/PenetrantTest/Introduction/Keywords/pt1.htm, 1 page, printed Aug. 13, 2003.

Capillary Force Lithography (CFL), Nano Precessing and Organic Devices Lab, 2 pages.

Capillary Rise of Liquid in Different Vanes Under Variable Residual Acceleration, http://www.zarm.uni-bremen.de/2forschung/grenzph/isoterm/cap_rise/kapst_en.htm, 2 pages, printed Jun. 24, 2003.

Chen et al., *The Kinetics of Wicking of Liquid Droplets into Yarns*, submitted to the Textile Research Journal, pp. 1-30.

Coating Techniques, Air Knife Coating, http://www.ferron-magnetic.co.uk/coatings/airknife.htm, 1 page, printed Jul. 1, 2003.

Coating Techniques, Gravure Coating, http://www.ferron-magnetic.co.uk/coatings/gravure.htm, 2 pages, printed Jul. 1, 2003.

Coating Techniques, Reverse Roll Coating, http://www.ferron-magnetic.co.uk/coatings/revroll.htm, 2 pages, printed Jul. 1, 2003.

Coating Techniques, Gap Coating, http://www.ferron-magnetic.co.uk/coatings/knife.htm, 1 page, printed Jul. 1, 2003.

Chung et al., *Inner core segment design for drug delivery control of thermo-responsive polymeric micelles*, Journal of Controlled Release 65:93-103 (2000).

Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).

Dichek et al., *Seeding of Intravascular Stents with Genetically Engineered Endothelial Cells*, Circ. 80(5):1347-1353 (Nov. 1989).

Dreyer et al., *Critical Velocities in Open Capillary Flows*, pp. 604-609.

Dutkiewicz, *Some Advances in Nonwoven Structures for Absorbency, Comfort and Aesthetics*, AUTEX Research Journal, vol. 2, No. 3, (Sep. 2002), pp. 153-165.

Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).

Erickson et al., *Numerical Simulations of Capillary-Driven Flows in Nonuniform Cross-Sectional Capillaries*, Journal of Colloid and Interface Science, vol. 250, pp. 422-430 (2002).

Fine Bubble Diffusers, Refractron Technologies Corp., 2 pages.

Helmus, *Overview of Biomedical Materials*, MRS Bulletin, pp. 33-38 (Sep. 1991).

Herdeg et al., *Antiproliferative Stent Coatings: Taxol and Related Compounds*, Semin. Intervent. Cardiol. 3:197-199 (1998).

Klocke et al, *How Soil Holds Water*, http://ianrpubs.unl.edu/fieldcrops/g964.htm, G90-964, 9 pages, printed Apr. 6, 2004.

Inoue et al., *An AB block copolymer of oligo(methyl methacrylate) and poly(acrylic acid) for micellar delivery of hydrophobic drugs*, Journal of Controlled Release 51:221-229 (1998).

Interfacial and Colloidal Phenomena Research Group, Illinois Institute of Technology, http://www.iit.edu/~wasan/exp1.html, 3 pages, printed Aug. 13, 2003.

Kataoka et al., *Block copolymer micelles as vehicles for drug delivery*, Journal of Controlled Release 24:119-132 (1993).

Konopka, *In-Plane Moisture Transport in Nonwovens*, Nonwovens Cooperative Research Center, 56 pages.

Levy et al., *Strategies For Treating Arterial Restenosis Using Polymeric Controlled Release Implants*, Biotechnol. Bioact. Polym. [Proc. Am. Chem. Soc. Symp.], pp. 259-268 (1994).

Liquid Gravity Motor, http://www.drspark86.com/idea001.html, 2 pages, printed Jun. 24, 2003.

Liu et al., *Drug release characteristics of unimolecular polymeric micelles*, Journal of Controlled Release 68:167-174 (2000).

Marconi et al., *Covalent bonding of heparin to a vinyl copolymer for biomedical applications*, Biomaterials 18(12):885-890 (1997).

Matsumaru et al., *Embolic Materials For Endovascular Treatment of Cerebral Lesions*, J. Biomater. Sci. Polymer Edn 8(7):555-569 (1997).

Miyazaki et al., *Antitumor Effect of Implanted Ethylene-Vinyl Alcohol Copolymer Matrices Containing Anticancer Agents of Ehrlich Ascites Carcinoma and P388 Leukemia in Mice*, Chem. Pharm. Bull. 33(6) 2490-2498 (1985).

Miyazawa et al., *Effects of Pemirolast and Tranilast on Intimal Thickening After Arterial Injury in the Rat*, J. Cardiovasc. Pharmacol., pp. 157-162 (1997).

Neimark et al., *Hierarchical Pore Structure and Wetting Properties of Single-Wall Carbon Nanotube Fibers*, Nano Letters, vol. 3, No. 3, pp. 419-423 (2003).

Nordrehaug et al., *A novel biocompatible coating applied to coronary stents*, European Heart Journal 14, p. 321 (P1694), Abstr. Suppl. (1993).

Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).

Ozaki et al., *New Stent Technologies*, Progress in Cardiovascular Diseases, vol. XXXIX(2):129-140 (Sep./Oct. 1996).

Pechar et al., *Poly(ethylene glycol) Multiblock Copolymer as a Carrier of Anti-Cancer Drug Doxorubicin*, Bioconjucate Chemistry 11(2):131-139 (Mar./Apr. 2000).

Peng et al., *Role of polymers in improving the results of stenting in coronary arteries*, Biomaterials 17:685-694 (1996).

Porosimetry, Why characterize the porosity, 42 pages.

Refractron Technologies Corp., http://www.refractron.com/ecom/sp/cat=Custom+Applications, 1 page, printed Jun. 24, 2003.

Refractron Advanced Porous Ceramic Product Capabilities, http://www.refractron.com/ecom/sp/cat=Product+Information, 3 pages, printed Apr. 6, 2004.

Shigeno, *Prevention of Cerebrovascular Spasm By Bosentan, Novel Endothelin Receptor*, Chemical Abstract 125:212307 (1996).

Straube, *Moisture, Materials, & Buildings,* HPAC Engineering, pp. 2-7.

Surface Energy (Surface Wetting Capability), http://www.ndt-ed.org/EducationResources/CommunityCollege/PenetrantTest/PTMaterials/surfaceenergy.htm, 3 pages, printed Apr. 6, 2004.

Taher et al., *Capillary Interaction Between a Small Thin Solid Plate and a Liquid,* 4 pages.

van Beusekom et al., *Coronary stent coatings,* Coronary Artery Disease 5(7):590-596 (Jul. 1994).

Vapor-Jet Capillary Pump—How it Works, Vapor Inc., http://www.vapore.com/tech_howto.htm, 2 pages, printed Aug. 13, 2003.

Viscosity, slides, 7 pages.

The Wicking Well System, http://www.decorative.com/wicking.html, 1 page, printed Jun. 24, 2003.

The 14th International Young Physicists Tournament, The winning report, Mgr. Martin Plesch, Research Center for Quantum Information, Slovak Academy of Sciences, Dubravska cesta 9, Bratislava, Slovakia, 5 pages.

Wilensky et al., *Methods and Devices for Local Drug Delivery in Coronary and Peripheral Arteries,* Trends Cardiovasc. Med. 3(5):163-170 (1993).

Yokoyama et al., *Characterization of physical entrapment and chemical conjugation of adriamycin in polymeric micelles and their design for in vivo delivery to a solid tumor,* Journal of Controlled Release 50:79-92 (1998).

Zhmud et al., *Dynamics of Capillary Rise,* Journal of Colloid and Interface Science, vol. 228, pp. 263-269 (2000).

\* cited by examiner

ABLUMINAL STENT COATING APPARATUS AND METHOD USING A BRUSH ASSEMBLY

TECHNICAL FIELD

This invention relates generally to stent coating apparatuses, and more particularly, but not exclusively, provides a brush assembly and method for coating of an abluminal stent surface.

BACKGROUND

Blood vessel occlusions are commonly treated by mechanically enhancing blood flow in the affected vessels, such as by employing a stent. Stents act as scaffoldings, functioning to physically hold open and, if desired, to expand the wall of affected vessels. Typically stents are capable of being compressed, so that they can be inserted through small lumens via catheters, and then expanded to a larger diameter once they are at the desired location. Examples in the patent literature disclosing stents include U.S. Pat. No. 4,733,665 issued to Palmaz, U.S. Pat. No. 4,800,882 issued to Gianturco, and U.S. Pat. No. 4,886,062 issued to Wiktor.

FIG. 1 illustrates a conventional stent 10 formed from a plurality of struts 12. The plurality of struts 12 are radially expandable and interconnected by connecting elements 14 that are disposed between adjacent struts 12, leaving lateral openings or gaps 16 between adjacent struts 12. The struts 12 and the connecting elements 14 define a tubular stent body having an outer, tissue-contacting surface and an inner surface.

Stents are being modified to provide drug delivery capabilities. A polymeric carrier, impregnated with a drug or therapeutic substance is coated on a stent. The conventional method of coating is by, for example, applying a composition including a solvent, a polymer dissolved in the solvent, and a therapeutic substance dispersed in the blend to the stent by immersing the stent in the composition or by spraying the composition onto the stent. The solvent is allowed to evaporate, leaving on the stent strut surfaces a coating of the polymer and the therapeutic substance impregnated in the polymer. The dipping or spraying of the composition onto the stent can result in a complete coverage of all stent surfaces, i.e., both luminal (inner) and abluminal (outer) surfaces, with a coating. However, having a coating on the luminal surface of the stent can have a detrimental impact on the stent's deliverability as well as the coating's mechanical integrity. Moreover, from a therapeutic standpoint, the therapeutic agents on an inner surface of the stent get washed away by the blood flow and typically can provide for an insignificant therapeutic effect. In contrast, the agents on the outer surfaces of the stent are in contact with the lumen, and provide for the delivery of the agent directly to the tissues. Polymers of a stent coating also elicit a response from the body. Reducing the amount to foreign material can only be beneficial.

Briefly, an inflatable balloon of a catheter assembly is inserted into a hollow bore of a coated stent. The stent is securely mounted on the balloon by a crimping process. The balloon is inflated to implant the stent, deflated, and then withdrawn out from the bore of the stent. A polymeric coating on the inner surface of the stent can increase the coefficient of friction between the stent and the balloon of a catheter assembly on which the stent is crimped for delivery. Additionally, some polymers have a "sticky" or "tacky" consistency. If the polymeric material either increases the coefficient of friction or adherers to the catheter balloon, the effective release of the stent from the balloon after deflation can be compromised. If the stent coating adheres to the balloon, the coating, or parts thereof, can be pulled off the stent during the process of deflation and withdrawal of the balloon following the placement of the stent. Adhesive, polymeric stent coatings can also experience extensive balloon sheer damage post-deployment, which could result in a thrombogenic stent surface and possible embolic debris. The stent coating can stretch when the balloon is expanded and may delaminate as a result of such shear stress.

Another shortcoming of the spray coating and immersion methods is that these methods tend to from defects on stents, such as webbing between adjacent stent struts 12 and connecting elements 14 and the pooling or clumping of coating on the struts 12 and/or connecting elements 14. In addition, spray coating can cause coating defects at the interface between a stent mandrel and the stent 10 as spray coating will coat both the stent 10 and the stent mandrel at this interface, possibly forming a clump. During removal of the stent 10 from the stent mandrel, this clump may detach from the stent 10, thereby leaving an uncoated surface on the stent 10. Alternatively, the clump may remain on the stent 10, thereby yielding a stent 10 with excessive coating.

Accordingly, a new apparatus and method are needed to enable selective coating of stent surfaces while minimizing the formation of defects.

SUMMARY

Embodiments of the invention provide an apparatus and method that enable selective coating of stent surfaces while avoiding coating defects caused by conventional spray coating and immersion coating techniques.

In an embodiment of the invention, that apparatus comprises a dispensing mechanism, a brush assembly in fluid communication with the dispensing mechanism, and an optical feedback system. The dispensing mechanism dispenses a coating onto the brush assembly and the optical feedback system aligns the brush assembly with a stent strut such that the brush assembly coats the stent strut with the dispensed coating.

It will be appreciated by one of ordinary skill in the art that the alignment can also be between the brush assembly and a connecting element in place of a stent strut. Accordingly, the use of the term strut or stent strut hereinafter also interchangeably refers to a connecting element.

In an embodiment of the invention, the method comprises: aligning a brush assembly with a stent strut, the brush assembly in fluid communication with a dispensing mechanism; and dispensing a coating from the dispensing mechanism onto the stent strut via the brush assembly.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

DETAILED DESCRIPTION

The following description is provided to enable any person having ordinary skill in the art to make and use the invention, and is provided in the context of a particular application and its requirements. Various modifications to the embodiments will be readily apparent to those skilled in the art, and the generic principles defined herein may be applied to other embodiments and applications without departing from the spirit and scope of the invention. Thus, the present invention is not intended to be limited to the embodiments shown, but is to be accorded the widest scope consistent with the principles, features and teachings disclosed herein.

Figure 1:
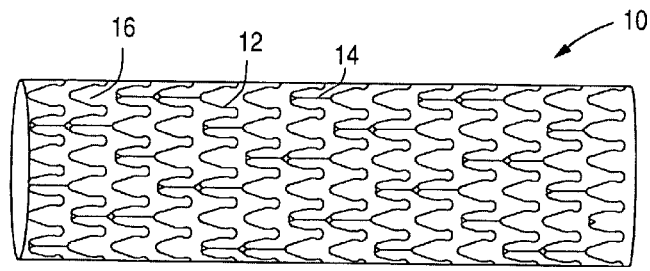
FIG. 1 is a diagram illustrating a conventional stent.
Figure 2:
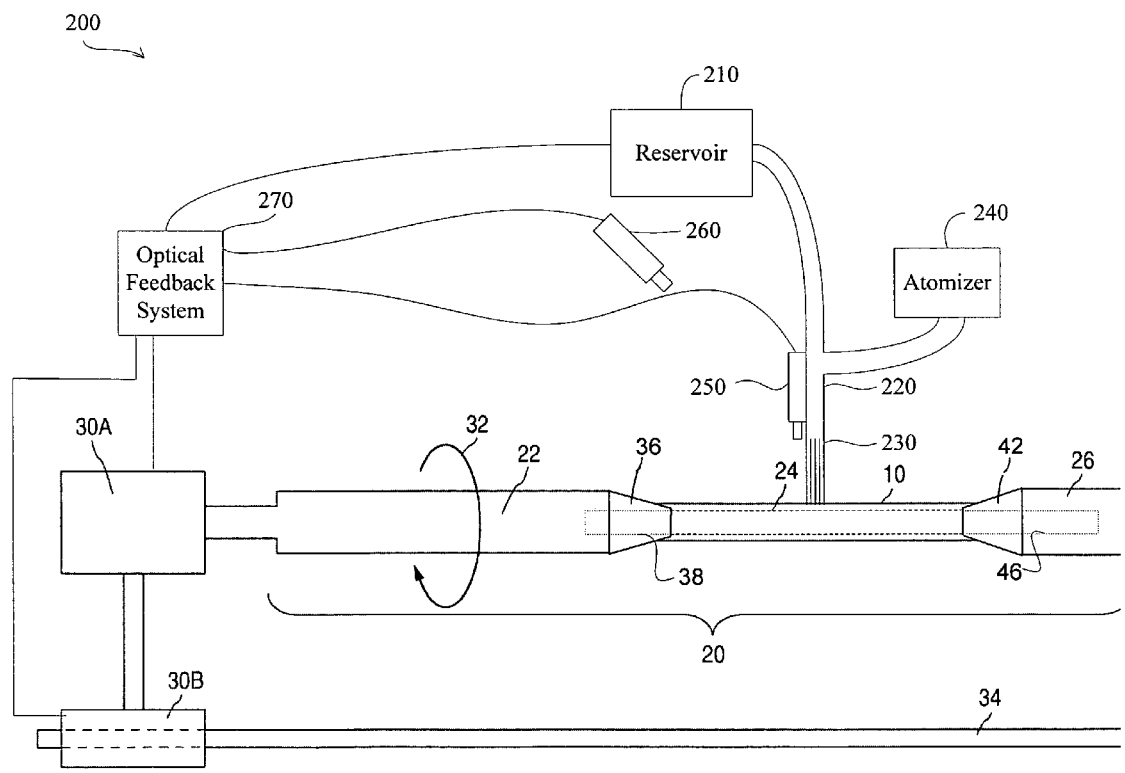
FIG. 2 is a block diagram illustrating a stent coating apparatus according to an embodiment of the invention.

FIG. 2 is a block diagram illustrating a stent coating apparatus 200 according to an embodiment of the invention. The apparatus 200, including a stent mandrel fixture 20 for supporting the stent 10, is illustrated to include a support member 22, a mandrel 24, and a lock member 26. The support member 22 can connect to a motor 30A so as to provide rotational motion about the longitudinal axis of the stent 10, as depicted by arrow 32, during a coating process. Another motor 30B can also be provided for moving the support member 22 in a linear direction, back and forth, along a rail 34.

The support member 22 includes a coning end portion 36, tapering inwardly. In accordance with one embodiment of the invention, the mandrel 24 can be permanently affixed to coning end portion 36. Alternatively, the support member 22 can include a bore 38 for receiving a first end of the mandrel 24. The first end of mandrel 24 can be threaded to screw into the bore 38 or, alternatively, can be retained within the bore 38 by a friction fit. The bore 38 should be deep enough so as to allow the mandrel 24 to securely mate with the support member 22. The depth of the bore 38 can also be over-extended so as to allow a significant length of the mandrel 24 to penetrate or screw into the bore 38. The bore 38 can also extend completely through the support member 22. This would allow the length of the mandrel 24 to be adjusted to accommodate stents of various sizes.

The lock member 26 includes a coning end portion 42 tapering inwardly. A second end of the mandrel 24 can be permanently affixed to the lock member 26 if the first end is disengageable from the support member 22. Alternatively, in accordance with another embodiment, the mandrel 24 can have a threaded second end for screwing into a bore 46 of the lock member 26. The bore 46 can be of any suitable depth that would allow the lock member 26 to be incrementally moved closer to the support member 22. The bore 46 can also extend completely through the lock member 26. Accordingly, the stents 10 of any length can be securely pinched between the support and the lock members 22 and 26. In accordance with yet another embodiment, a non-threaded second end and the bore 46 combination is employed such that the second end can be press-fitted or friction-fitted within the bore 46 to prevent movement of the stent 10 on the stent mandrel fixture 20.

Positioned a distance from the stent 10 (e.g., above the stent 10) is a reservoir 210 holding a coating substance to be applied to the stent 10. The reservoir 210 is in fluid communication with a needle or other dispensing mechanism 220, which is in fluid communication with a brush assembly 230. In an embodiment of the invention, an atomizer 240 can be coupled to the needle 220 and provides atomizing air to the needle 220 for atomizing the coating substance before it is dispensed.

The reservoir 210 dispenses the coating substance to the needle 220, which dispenses it to the brush assembly 230, which will be discussed in further detail in conjunction with FIGS. 4A-4F below. The reservoir 210 can dispense the coating substance using gravity and/or forced pressure (e.g., a pump). The use of forced pressure enables the accurate control of the amount of coating substance dispensed. The force must be high enough to allow for the adequate coating of the stent 10 but cannot to be too high such that it leads to non-uniform coating of the stent 10. The reservoir 210 can dispense the coating at a constant rate, at a variable rate, or intermittently. For example, during the application of the coating substance, the rate of coating dispensed can be adjusted so that certain sections of the stent 10 receive more coating than others. If the coating material is applied in an intermittent fashion, coating adjustments can be made during the stoppage of coating application. Further, the coating can be stopped while the brush assembly 230 is being repositioned relative to the stent 10. Negative pressure can be applied to the brush assembly 230 to prevent the coating from inadvertently dripping onto the stent 10.

The brush assembly 230 is aligned with a stent strut 12 and coats each individual stent strut 12. As will be discussed further below in conjunction with FIG. 5, coating flows from the needle 220 to and along the brush assembly 230 onto the stent strut 12, thereby limiting the coating to just the outer surface stent strut 12 and not other surfaces (e.g., the luminal surface) as in spaying and immersion techniques. In one embodiment, the sidewalls of the stent struts 12 between the outer and inner surfaces can be partially coated. Partial coating of sidewalls can be incidental, such as that some coating can flow from the outer surface onto the sidewalls. In some embodiments coating of sidewalls can be intentional, such that the brush is designed to deposit coating on the other surfaces. In some embodiment, the brush is designed to completely coat all of the sidewalls of the struts 12.

Coupled to the needle 220 can be a first imaging device 250 that images the stent 10 before and/or after the coating substance has been applied to a portion of the stent 10. The first imaging device 250, along with a second imaging device 260 located a distance from the stent 10, are both communicatively coupled to an optical feedback system 270 via wired or wireless techniques. The reservoir 210 and the atomizer 240 may also be communicatively coupled to the optical feedback system 270 via wired or wireless techniques. Based on the imagery provided by the imaging devices 250 and 260, the optical feedback system 270 controls movement of stent 10 via the motors 30A and 30B to keep the brush assembly 230 aligned with the stent struts 12 and recoat the stent struts 12 if improperly (or inadequately) coated.

During operation of the stent coating apparatus 200, the optical feedback system 270 causes the imaging device 260 to image the full surface of the stent 10 as the feedback system 270 causes the motor 30A to rotate the stent 10. After the initial imaging, the optical feedback system 270, using the imaging device 260, aligns the brush assembly 230 with a stent strut 12 by causing the engines 30A and 30B to rotate and translate the stent 10 until alignment is achieved. The optical feedback system 270 then causes the reservoir 210 (e.g., through a pump mechanism known to those of ordinary skill in the art) to dispense the coating substance through the needle 220 to the brush assembly 230. As the coating substance is dispensed, the optical feedback system 270 causes the engines 30A and 30B to rotate and translate the stent 10 in relation to the brush assembly 230 so as to effective drag the stent strut 12 along the brush assembly 230, thereby causing the strut 12 to be coated. In an embodiment of the invention, the optical feedback system 270 also cause the atomizer 240 to atomize the coating substance as it is being dispensed through the needle 220.

After a portion of the stent strut 12 has been coated, the optical feedback system 270 causes the reservoir 210 to cease dispensing the coating substance and causes the imaging device 250 to image the stent strut 12 to determine if the strut 12 has been adequately coated. This determination can be made by measuring the difference in color and/or reflectivity of the stent strut 12 before and after the coating process. If the strut 12 has been adequately coated, then the optical feedback system 270 causes the engines 30A and 30B to rotate and translate the stent 10 so that the brush assembly 230 is aligned with an uncoated stent 10 section and the above process is then repeated. If the stent strut 12 is not coated adequately, then the optical feedback system 270 causes the engines 30A and 30B to rotate and translate the stent 10 and the reservoir 210 to dispense the coating substance to recoat the stent strut 12. In another embodiment of the invention, the optical feedback system 270 can cause checking and recoating of the stent 10 after the entire stent 10 is goes through a first coating pass.

In an embodiment of the invention, the imaging devices 250 and 260 include charge coupled devices (CCDs) or complementary metal oxide semiconductor (CMOS) devices. In an embodiment of the invention, the imaging devices 250 and 260 are combined into a single imaging device. Further, it will be appreciated by one of ordinary skill in the art that placement of the imaging devices 250 and 260 can vary as long as they have an acceptable view of the stent 10. In addition, one of ordinary skill in the art will realize that the stent mandrel fixture 20 can take any form or shape as long as it is capable of securely holding the stent 10 in place.

Accordingly, embodiments of the invention enable the fine coating of specific surfaces of the stent 10, thereby avoiding coating defects that can occur with spray coating and immersion coating methods and limiting the coating to only the abluminal surface and/or sidewalls of the stent 10. Application of the coating in the gaps 16 between the stent struts 12 can be partially, or preferable completely, avoided.

After the brush coating of the stent 10 abluminal surface, the stent 10 can then have the inner surface coated via electroplating or spray coating. Without masking the outer surface of the stent 10, both electroplating and spray coating may yield some composition onto the outer surface and sidewalls of the stent 10. However, the inner surface would be substantially solely coated with a single composition different from the composition used to coat the outer surface of the stent 10. Accordingly, it will be appreciated by one of ordinary skill in the art that this embodiment enables the coating of the inner surface and the outer surface of the stent 10 with different compositions. For example, the inner surface could be coated with a composition having a bio-beneficial therapeutic substance for delivery downstream of the stent 10 (e.g., an anticoagulant, such as heparin, to reduce platelet aggregation, clotting and thrombus formation) while the outer surface of the stent 10 could be coating with a composition having a therapeutic substance for local delivery to a blood vessel wall (e.g., an anti-inflammatory drug to treat vessel wall inflammation or a drug for the treatment of restenosis).

The components of the coating substance or composition can include a solvent or a solvent system comprising multiple solvents, a polymer or a combination of polymers, a therapeutic substance or a drug or a combination of drugs. In some embodiments, the coating substance can be exclusively a polymer or a combination of polymers (e.g., for application of a primer layer or topcoat layer). In some embodiments, the coating substance can be a drug that is polymer free. Polymers can be biostable, bioabsorbable, biodegradable, or bioerodible. Biostable refers to polymers that are not biodegradable. The terms biodegradable, bioabsorbable, and bioerodible are used interchangeably and refer to polymers that are capable of being completely degraded and/or eroded when exposed to bodily fluids such as blood and can be gradually resorbed, absorbed, and/or eliminated by the body. The processes of breaking down and eventual absorption and elimination of the polymer can be caused by, for example, hydrolysis, metabolic processes, bulk or surface erosion, and the like.

Representative examples of polymers that may be used include, but are not limited to, poly(N-acetylglucosamine) (Chitin), Chitoson, poly(hydroxyvalerate), poly(lactide-co-glycolide), poly(hydroxybutyrate), poly(hydroxybutyrate-co-valerate), polyorthoester, polyanhydride, poly(glycolic acid), poly(glycolide), poly(L-lactic acid), poly(L-lactide), poly(D,L-lactic acid), poly(D,L-lactide), poly(D-lactic acid), poly(D-lactide), poly(caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose. Representative examples of polymers that may be especially well suited for use include ethylene vinyl alcohol copolymer (commonly known by the generic name EVOH or by the trade name EVAL), poly(butyl methacrylate), poly(vinylidene fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol.

"Solvent" is defined as a liquid substance or composition that is compatible with the polymer and/or drug and is capable of dissolving the polymer and/or drug at the concentration desired in the composition. Examples of solvents include, but are not limited to, dimethylsulfoxide, chloroform, acetone, water (buffered saline), xylene, methanol, ethanol, 1-propanol, tetrahydrofuran, 1-butanone, dimethylformamide, dimethylacetamide, cyclohexanone, ethyl acetate, methylethylketone, propylene glycol monomethylether, isopropanol, isopropanol admixed with water, N-methylpyrrolidinone, toluene, and mixtures and combinations thereof.

The therapeutic substance or drug can include any substance capable of exerting a therapeutic or prophylactic effect. Examples of active agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. The bioactive agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel, (e.g., TAXOL® by Bristol-Myers Squibb Co., Stamford, Conn.), docetaxel (e.g., Taxotere®, from Aventis S.A., Frankfurt, Germany), methotrexate, azathioprine, vincristine, vinblastine, fluorouracil, doxorubicin hydrochloride (e.g., Adriamycin® from Pharmacia & Upjohn, Peapack N.J.), and mitomycin (e.g., Mutamycin® from Bristol-Myers Squibb Co., Stamford, Conn.). Examples of such antiplatelets, anticoagulants, antifibrin, and antithrombins include aspirin, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax ä (Biogen, Inc., Cambridge, Mass.). Examples of such cytostatic or antiproliferative agents include angiopeptin, angiotensin converting enzyme inhibitors such as captopril (e.g., Capoten® and Capozide® from Bristol-Myers Squibb Co., Stamford, Conn.), cilazapril or lisinopril (e.g., Prinivil® and Prinzide® from Merck & Co., Inc., Whitehouse Station, N.J.), calcium channel blockers (such as nifedipine), colchicine, proteins, peptides, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate agents include cisplatin, insulin sensitizers, receptor tyrosine kinase inhibitors, carboplatin, alpha-interferon, genetically engineered epithelial cells, steroidal anti-inflammatory agents, non-steroidal anti-inflammatory agents, antivirals, anticancer drugs, anticoagulant agents, free radical scavengers, estradiol, antibiotics, nitric oxide donors, super oxide dismutases, super oxide dismutases mimics, 4-amino-2,2,6,6-tetramethylpiperidine-1-oxyl (4-amino-TEMPO), tacrolimus, dexamethasone, ABT-578, clobetasol, cytostatic agents, prodrugs thereof, co-drugs thereof, and a combination thereof. Other therapeutic substances or agents may include rapamycin and structural derivatives or functional analogs thereof, such as 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin.

Figure 3:
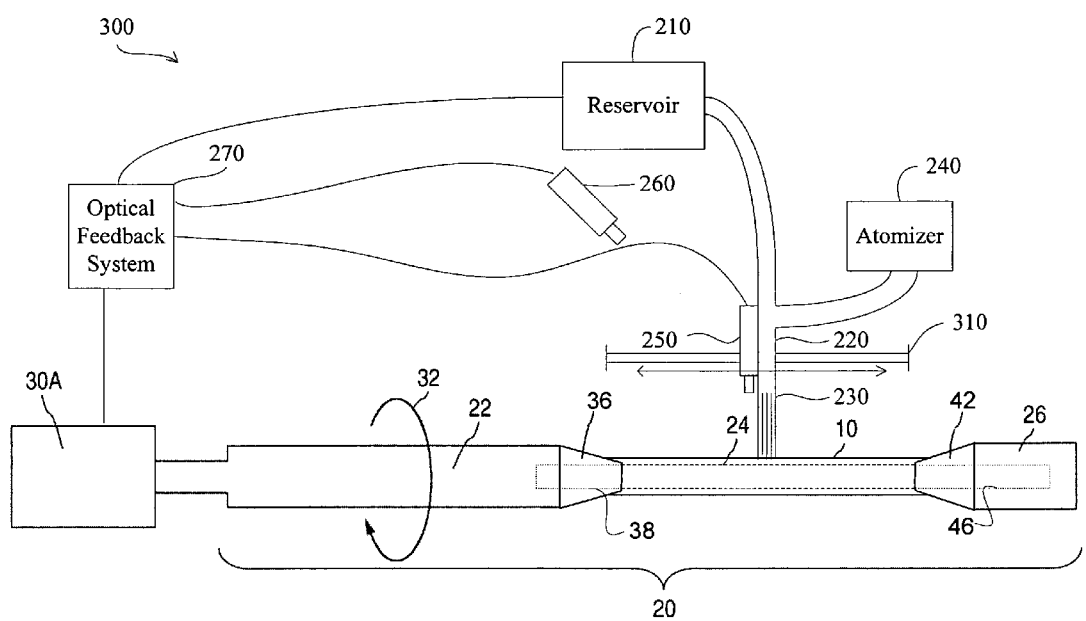
FIG. 3 is a block diagram illustrating a stent coating apparatus according to another embodiment of the invention.

FIG. 3 is a block diagram illustrating a stent coating apparatus 300 according to another embodiment of the invention. The stent coating apparatus 300 is similar to the stent coating apparatus 200. However, the brush assembly 230 is capable of translational movement along a guide rail 310. Accordingly, the alignment of the brush assembly 230 with a stent strut 12 is accomplished by the optical feedback system 270 causing the engine 30A to rotate the stent 10 in combination with causing the brush assembly 230 to move along the guard rail 310. The guard rail 310 should be at least about as long as the stent 10 to enable the brush assembly 230 full mobility over the length of the stent 10. In some embodiments, the brush assembly 230 is capable of translational movement along the guide rail 310 in combination with rotation and translation of the stent 10.

In another embodiment of the invention, the brush assembly 230 is coupled to a painting robot, such as one have six axes (three for the base motions and three for applicator orientation) that incorporates machine vision and is electrically driven. Accordingly, the brush assembly 230 can fully rotate around and translate along a stent 10 in a stationary position. Alternatively, both the brush assembly 230 and the stent 10 can rotate and/or translate. For example, the brush assembly 230 can move for alignment with a strut of the stent 10 while the stent 10 can move during coating after alignment, vice versa, or a combination of both.

In any of the above-mentioned embodiments, the coating process can be continuous, i.e., the brush assembly 230 can move along and coat the entire stent 10 without lifting off of the stent, or move intermittently, i.e., coating a first section of the stent 10, optionally lifting off and then aligning with a second section of the stent 10, and coating that second section. The second section may be adjacent to the first section or located a distance from the first section.

FIG. 4A, FIG. 4B, FIG. 4C, FIG. 4D, FIG. 4E, and FIG. 4F are diagrams illustrating the brush assemblies 230a-230d of the stent coating apparatuses 200 and 300 according to embodiments of the invention. The brush assembly 230a of FIG. 4A can be coupled to a brush module 400 that can be coupled to a mouth of the needle 220. The brush module 400 comprises a spongy or porous material that enables a coating substance to travel through the module 400 (e.g., a mesh plate) onto the brush assembly 230a. The brush assembly 230a comprises a plurality of fibers or bristles made of any suitable material that enables the flow of the coating substance. In an embodiment of the invention, the bristles can be made from polymer (e.g., rubber), glass, pig bristle, metal fibers, ultra-fine non-absorbent or absorbent fibers, etc. The fibers of the brush assembly 230a can be coupled to the module 400 by stringing the fibers through the pores of the module 400. In another embodiment of the invention, the fibers can be inserted directly into the mouth of the needle 220 without a module 400 and the mouth of the needle 220 is then mechanically compressed to hold the fibers in place. Any component including the needle 220, brush module 400 and brush assembly 230 can be disposable so as to allow a user to use different materials, for example for construction of a tri-layer coating such that at least two of the primer, drug/polymer, and topcoat layers are made from different materials.

The number of fibers in the brush assembly 230a can vary from a single fiber (e.g., the brush assembly 230b having a single fiber centered in the mouth of the needle 220) to a plurality of fibers (e.g., hundreds). The lengths of the fibers vary based on the length of the stent strut 12. The length, number, and fiber material also vary based on the viscosity of the coating substance, the rate of application, the pattern of the stent, among other factors. The fibers can be long enough such that during the brush process, the fibers can drag along the surface being coated. Alternatively, the fibers can be short enough so as to be less pliable to prevent bending or dragging the fibers. A combination of the two embodiments can also be used. For example, the fibers on opposing edges can be long enough to drag on the sidewalls while the fibers on the middle segment are thicker or made from more rigid material so as to prevent dragging of the fibers during the application process. Alternatively, the fibers of middle segment can be more pliant while the fibers at the opposing edges can be rigid.

In an embodiment of the invention, fiber length varies from about ⅛ inch to about 1 inch. In one embodiment, the fiber diameter is about 0.004 inches. As shown in FIGS. 4D-FIG. 4F, the length of the fibers in the brush assembly 230d can vary from each other. Accordingly, when the needle 220 is aligned with stent strut 12, longer fibers extend down the sidewalls of the stent strut 12 while shorter fibers extend along the outside surface of the stent strut 12, thereby enabling coating of both the outer surface and the sidewalls of the stent strut 12. For example, as shown in FIG. 4E, a cross section of the needle 220 with brush assembly 230*d* is shown. The lengths of the fibers are represented by their diameter and as such, fibers aligned with the sidewalls of the strut 12 are longer than fibers aligned with the abluminal surface of the strut 12. (The diameters of the fibers in FIG. 4E do not represent the relative width of the fibers although in some embodiments, widths of the fibers can be different).

Referring in more detail to FIGS. 4E and 4F, as best illustrated, the area populated by shorter fibers of the middle portion of the brush assembly 230*d* are bounded by the longer fibers at two of the end regions of the brush assembly 230*d*, which in effect provides a passageway or channel through the brush assembly 230*d*. The width of this channel can be designed so as to be equivalent or generally equivalent to the width of a strut being coating. Accordingly, during the coating process, a strut fits between the longer fibers as the brush is guided across the strut. With interchangeable components, a user can select a brush that is compatible with a width of a given strut.

Figure 4A:
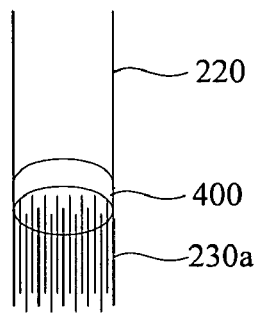
FIG. 4A, FIG. 4B, FIG. 4C, FIG. 4D, FIG. 4E, and FIG. 4F are diagrams illustrating brush assemblies of the stent coating apparatuses according to embodiments of the invention.
Figure 4B:
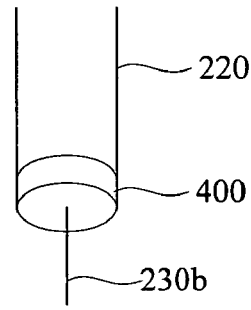
Figure 4C:
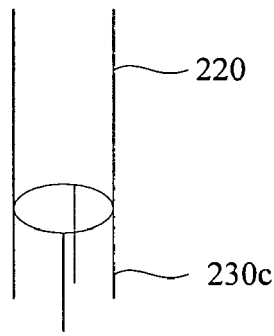
Figure 4D:
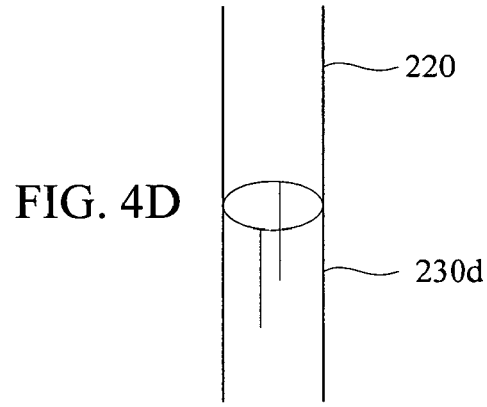
Figure 4E:
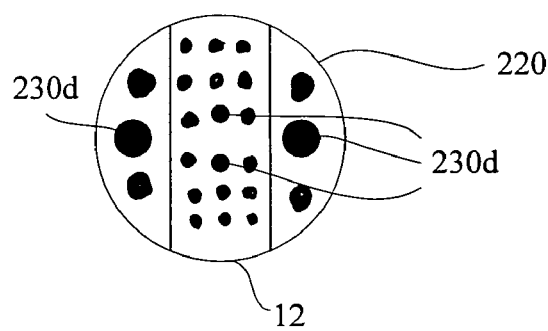
Figure 4F:
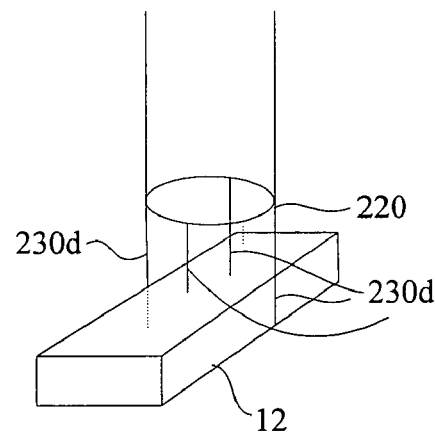

As shown in FIG. 4C and FIG. 4D, embodiments of the invention can include brush assemblies 230*c* and 230*d* wherein fibers of the assemblies are solely attached to perimeter (circumference) of the needle 220 mouth. Accordingly, the module 400 is not required. In an embodiment of the invention, a brush assembly can include fibers coupled to both a module 400 and to the perimeter of the needle 220 mouth.

Figure 5:
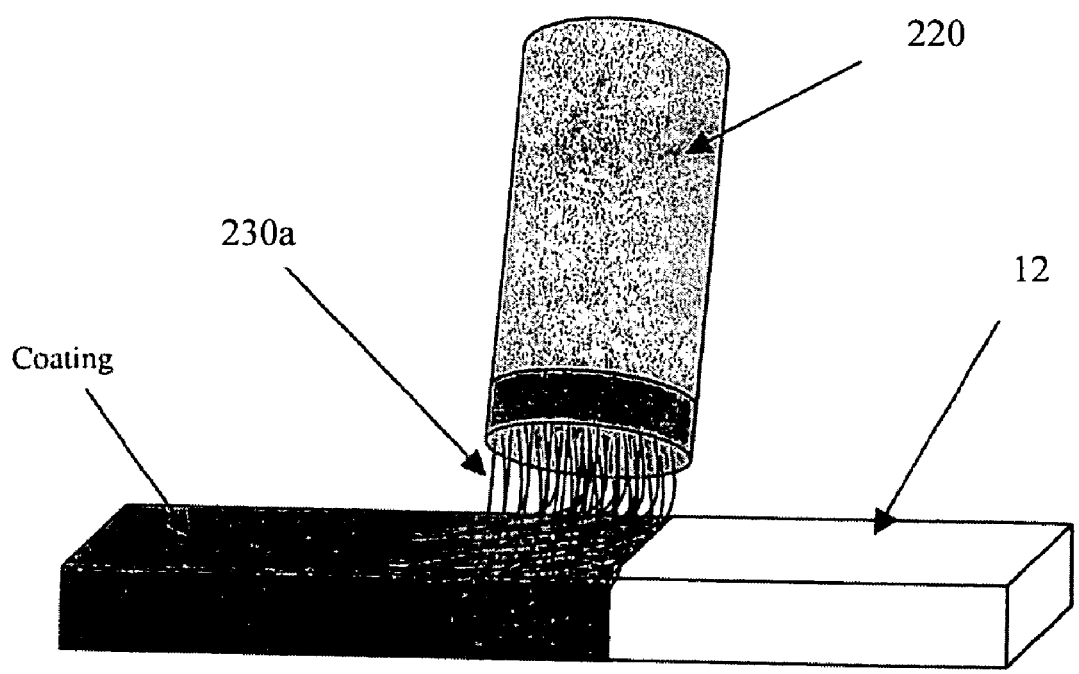
FIG. 5 is a diagram illustrating a brush assembly coating a stent strut.

FIG. 5 is a diagram illustrating the brush assembly 230*a* coating a stent strut 12. During operation of the system 200 or 300, the optical feedback system 270 causes the alignment of the needle 220 with a stent strut 12. The optical feedback system 270 then causes the reservoir 210 to dispense a coating substance to the needle 220 to the brush assembly 230*a*. In addition, the optical feedback system 270 can also cause the atomizer 240 to supply atomizing air to the needle 220 during dispensing of the coating substance.

In an embodiment of the invention, the brush assembly 230*a* is aligned with the stent strut 12 such that fibers of the brush assembly 230*a* extend along the full depth of the sidewalls of the strut 12, thereby enabling coating of the stent strut 12 abluminal surface as well as the sidewalls. In another embodiment of the invention, the needle 220 is positioned so that the fibers of the brush assembly 230*a* only extend to the abluminal surface of the stent strut 12, thereby coating only the abluminal stent strut 12 surface and not the sidewalls of the stent strut 12.

Further, as can be seen in FIG. 5, the coating can produce a different color on the stent strut 12, thereby enabling the optical feedback system 270 to determine if the strut 12 has not been adequately coated based on a color change. In an alternative embodiment of the invention, the optical feedback system 270 can measure a change in reflectivity of the stent strut 12 and/or other parameters.

Figure 6:
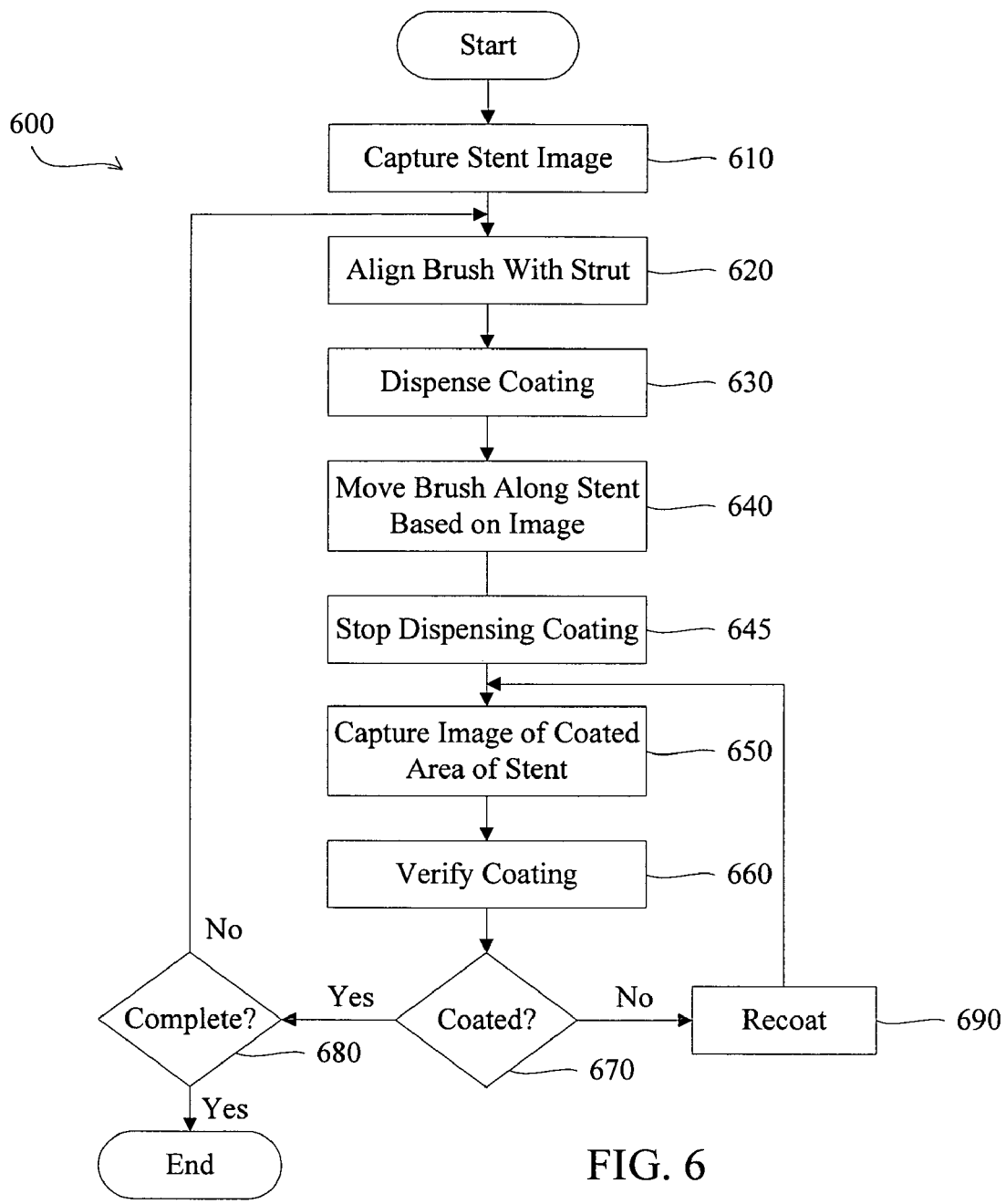
FIG. 6 is a flowchart illustrating a method of coating an abluminal stent surface.

FIG. 6 is a flowchart illustrating a method 600 of coating an abluminal stent surface. In an embodiment of the invention, the system 200 or 300 can implement the method 600. First, an image of the stent 10 is captured (610) as the stent 10 is rotated. Based on the captured image, a brush is aligned (620) with a stent strut 12 of the stent 10 via rotation and/or translation of the stent 10 and/or translation of the brush. A coating is then dispensed (630) onto the brush. In an embodiment of the invention, during the dispensing (630), the coating can also be atomized. As the coating is being dispensed (630), the brush and/or stent are moved (640) relative to each other so as to coat at least a portion of the stent strut 12.

The dispensing is then stopped (645), and an image of at least a portion of the stent that was just coated in captured (650). Using the captured image, the coating is verified (660) based on color change, reflectivity change, and/or other parameters. If (670) the coating is not verified (e.g., the stent strut 12 was not fully coated), then the strut 12 is recoated (690) by realigning the brush with the strut 12, dispensing the coating, and moving the brush relative to the strut. Capturing (650) an image and verifying (660) are then repeated.

If (670) the coating is verified and if (680) the stent has been completely coated, then the method 600 ends. Otherwise, the method 600 is repeated with a different stent strut starting with the aligned (620).

In an embodiment of the invention, the luminal surface of the stent 10 can then be coating with a different coating using electroplating or other technique. Accordingly, the abluminal surface and the luminal surface can coated with different coatings.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A stent coating apparatus, comprising:
   a stent support configured for supporting a stent, the stent having ends and an interior, the stent support comprising:
   a first support member;
   a second support member; and
   a third member extending between the first and second support members;
   wherein the first and second support members are configured to support the stent at only the stents ends; and
   wherein the third support member is configured to extend through the interior of the stent and is configured to support the stent at only the ends of the stent;
   a brush assembly on a brush assembly support;
   a dispensing mechanism in fluid communication with the brush assembly to dispense a coating onto the brush assembly; and
   an optical feedback system that is configured and arranged to effect alignment between the brush assembly and a stent strut, via relative movement between the stent support and the brush assembly support, such that the brush assembly coats the stent strut with the dispensed coating.

2. The apparatus of claim 1, wherein the optical feedback system is configured and arranged to verify the coating on the stent strut and is configured and arranged to effect recoating of the stent strut if the coating is determined to be inadequate.

3. The apparatus of claim 1, wherein the brush assembly has a first portion and a second portion, wherein the first portion has fibers of a first length or fiber stiffness substantially contained therein, and the second portion has fibers of a second length or fiber stiffness substantially contained therein.

4. The apparatus of claim 3, wherein the brush assembly comprises an area populated by shorter fibers in the middle portion of the brush assembly bounded by longer fibers at two of the end regions of the brush assembly such that a channel is formed through the brush assembly, wherein the width of the channel is equivalent or generally equivalent to the width of a stent strut to be coated.

5. The apparatus of claim 4, wherein for the brush assembly the fibers in the middle portion are more pliant than the fibers at the two end regions.

6. The apparatus of claim 4, wherein for the brush assembly the fibers in the middle portion are more rigid than the fibers at the two end regions.

7. The apparatus of claim 3, wherein the first portion is a middle portion and the second portion is an end portion.

8. The apparatus of claim 1, wherein the brush assembly includes at least one fiber in fluid communication with a mouth of the dispensing mechanism via a porous module.

9. The apparatus of claim 1, wherein the brush assembly includes at least one fiber fixed to a perimeter of a mouth of the dispensing mechanism.

10. The apparatus of claim 1, wherein the stent support is configured and arranged to rotate and translate the stent and the optical feedback system is configured and arranged to effect alignment of the brush assembly with the stent strut via rotation and translation of the stent.

11. The apparatus of claim 1, wherein the stent support is configured and arranged to rotate the stent, the brush assembly support is configured and arranged to translate the brush assembly and the optical feedback system is configured and arranged to effect alignment of the brush assembly with the stent strut via rotation of the stent and translation of the brush assembly.

12. The apparatus of claim 1, wherein the optical feedback system comprises at least one imaging device, the at least one image device comprising a charge coupled device, a complementary metal oxide semiconductor, or both.

13. The apparatus of claim 1, further comprising an atomizer coupled to the dispensing mechanism.

14. The apparatus of claim 1, wherein the first support member is configured for being selectively moveable relative to the second support member so as to enable the support to secure the stent by pinching the stent between the support members.

15. The apparatus of claim 1, wherein the first support member has a tapered portion and the second support member has a tapered portion, and wherein the first and second support members are configured to support the stent on the tapered portions.

16. The apparatus of claim 1, wherein the optical feedback system is configured and arranged to effect alignment between the brush assembly and the stent strut such that both an abluminal surface and sidewalls of the stent strut are coated.

17. The apparatus of claim 1, wherein the optical feedback system is configured and arranged to effect alignment between the brush assembly and the stent strut such that only the abluminal surface of the stent strut is coated and not the sidewalls of the stent strut.

18. The apparatus of claim 1, wherein the optical feedback system is configured and arranged to effect relative movement between the brush assembly and the stent strut while the coating is being dispensed.

19. A stent coating apparatus, comprising:
means for supporting a stent wherein the support means is configured to support the stent at only the stent ends and part of the support means is configured to extend through the interior of the stent;
means for supporting a brush assembly;
means for aligning and moving the brush assembly and a stent strut relative to each other, the brush assembly in fluid communication with a dispensing mechanism; and
means for dispensing a coating from the dispensing mechanism onto the aligned stent strut via the brush assembly.

20. A combination of a stent coating apparatus and a stent, comprising:
a stent, the stent having ends and an interior;
a stent support that supports the stent, the stent support comprising:
a first support member;
a second support member; and
a third member extending between the first and second support members;
wherein the first and second support members support the stent at only the stents ends; and
wherein the third support member extends through the interior of the stent and supports the stent at only the ends of the stent;
a brush assembly on a brush assembly support;
a dispensing mechanism in fluid communication with the brush assembly to dispense a coating onto the brush assembly; and
an optical feedback system that is configured and arranged to effect alignment between the brush assembly and a strut of the stent, via relative movement between the stent support and the brush assembly support, such that the brush assembly coats the stent strut with the dispensed coating.

21. The combination of the stent coating apparatus and stent of claim 20, wherein the brush assembly comprises an area populated by shorter fibers in the middle portion of the brush assembly bounded by longer fibers at two of the end regions of the brush assembly such that a channel is formed through the brush assembly, wherein the width of the channel is equivalent or generally equivalent to the width of the stent strut.

22. The combination of the stent coating apparatus and stent of claim 21, wherein the brush assembly comprises fibers extending along the depth of the sidewall of the strut such that the brush assembly is capable of coating both the sidewalls and the abluminal surface of the stent strut with the dispensed coating.

23. The combination of the stent coating apparatus and stent of claim 21, wherein for the brush assembly the fibers in the middle portion are more pliant than the fibers at the two end regions.

24. The combination of the stent coating apparatus and stent of claim 21, wherein for the brush assembly the fibers in the middle portion are more rigid than the fibers at the two end regions.

* * * * *

UNITED STATES PATENT AND TRADEMARK OFFICE
CERTIFICATE OF CORRECTION

PATENT NO. : 7,588,642 B1  Page 1 of 1
APPLICATION NO. : 10/999829
DATED : September 15, 2009
INVENTOR(S) : Morris et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 952 days.

Signed and Sealed this

Twenty-first Day of September, 2010

David J. Kappos
*Director of the United States Patent and Trademark Office*